US012156586B2

(12) United States Patent
Mast (10) Patent No.: US 12,156,586 B2
(45) Date of Patent: Dec. 3, 2024

(54) DEVICE FOR ASSISTANCE IN CARRYING LOADS

(71) Applicant: HUNIC GmbH, Baiersbronn (DE)

(72) Inventor: Jonas Mast, Baiersbronn (DE)

(73) Assignee: HUNIC GmbH, Baiersbronn (DE)

( * ) Notice: Subject to any disclaimer, the term of this patent is extended or adjusted under 35 U.S.C. 154(b) by 16 days.

(21) Appl. No.: 17/969,386

(22) Filed: Oct. 19, 2022

(65) Prior Publication Data

US 2023/0131059 A1    Apr. 27, 2023

(30) Foreign Application Priority Data

Oct. 21, 2021 (DE) ...................... 10 2021 127 397.8

(51) Int. Cl.
*B65G 7/12* (2006.01)
*A45F 5/00* (2006.01)

(52) U.S. Cl.
CPC . *A45F 5/00* (2013.01); *B65G 7/12* (2013.01)

(58) Field of Classification Search
CPC ....................................................... B65G 7/12
USPC ............. 224/270, 660–684; 108/43; D3/215; D24/190; 602/19; 2/44
See application file for complete search history.

(56) References Cited

U.S. PATENT DOCUMENTS

| 947,024 | A | * | 1/1910 | Priest | A45F 5/00 |
| | | | | | 224/907 |
| 2,945,614 | A | * | 7/1960 | Wittmann | B44D 3/14 |
| | | | | | 224/618 |
| 4,211,219 | A | * | 7/1980 | Alvey | A45F 5/00 |
| | | | | | 128/95.1 |
| 4,319,704 | A | * | 3/1982 | Rosen | A45F 5/02 |
| | | | | | 224/907 |
| 4,901,898 | A | * | 2/1990 | Colombo | A47D 13/029 |
| | | | | | 224/159 |

(Continued)

FOREIGN PATENT DOCUMENTS

| DE | 29913362 | 1/2000 |
| DE | 202005017186 | 1/2006 |

(Continued)

OTHER PUBLICATIONS

European Search Report issued on Feb. 17, 2023 in EP22202047.1 (with machine generated English Translation).

(Continued)

*Primary Examiner* — Justin M Larson
(74) *Attorney, Agent, or Firm* — Akerman LLP; Peter A. Chiabotti (57) ABSTRACT

A device for load bearing support with a hip belt with an inner side for application in contact on the body of a person, and an outer side, with a first end and a second end which are connectable with one another by means of a closure element, wherein the hip belt comprises a back element for application in contact on a section of the back of the person, and wherein on the back element a first hip belt section is disposed, wherein on the outer side of the first hip belt section at least one, outwardly projecting first deposition element or elements is or are disposed at such distance from the back element that in condition of application in contact on the body of the person it is or they are disposed laterally on the body of the person.

15 Claims, 12 Drawing Sheets

(56) References Cited

U.S. PATENT DOCUMENTS

| | | | | |
|---|---|---|---|---|
| 5,228,609 | A * | 7/1993 | Gregory | A45F 3/02 224/907 |
| 5,232,424 | A * | 8/1993 | Pearson | A61F 5/028 482/106 |
| D358,215 | S * | 5/1995 | Reed | D24/190 |
| 5,433,697 | A * | 7/1995 | Cox | A61F 5/028 602/19 |
| 5,511,707 | A * | 4/1996 | Reichert | A45F 5/00 224/678 |
| 5,570,824 | A * | 11/1996 | Lyon | A45F 5/021 224/678 |
| 5,609,283 | A * | 3/1997 | Harrison, Jr. | A45F 5/02 224/678 |
| 5,826,763 | A * | 10/1998 | Roberts | A45F 3/14 224/270 |
| 5,941,436 | A * | 8/1999 | Washington | A45F 3/14 224/259 |
| 5,950,886 | A * | 9/1999 | Maupin | A61G 1/04 224/660 |
| 6,053,383 | A * | 4/2000 | Gunderson | A45F 3/14 224/664 |
| 6,068,606 | A * | 5/2000 | Castel | A41D 13/0525 602/19 |
| 6,137,675 | A | 10/2000 | Perkins | |
| 6,216,931 | B1 * | 4/2001 | Trawinski | A45F 3/14 224/904 |
| 6,390,348 | B1 * | 5/2002 | Godshaw | B25H 3/00 224/660 |
| 6,634,533 | B2 * | 10/2003 | Thompson | A45F 3/047 224/663 |
| D484,296 | S * | 12/2003 | Newman | D2/627 |
| 6,766,532 | B1 * | 7/2004 | Cabana | A61F 5/028 2/310 |
| D504,992 | S * | 5/2005 | Taylor | D2/639 |
| 6,893,098 | B2 * | 5/2005 | Kohani | A47C 7/425 297/468 |
| D507,692 | S * | 7/2005 | Newman | D2/627 |
| 7,165,706 | B2 * | 1/2007 | Barr | A45F 5/021 224/672 |
| 7,201,299 | B2 * | 4/2007 | Forsman | A45F 3/14 224/148.2 |
| 7,329,231 | B2 * | 2/2008 | Frank | A61F 5/028 602/19 |
| 7,762,440 | B2 * | 7/2010 | Cook | A45F 5/021 224/660 |
| 7,891,023 | B1 * | 2/2011 | Hill | A41F 3/00 2/310 |
| 8,235,925 | B2 * | 8/2012 | Cavalieri | A61F 5/028 128/845 |
| 8,449,484 | B2 * | 5/2013 | Johnson | A61F 5/30 602/18 |
| 9,044,081 | B2 * | 6/2015 | McDonald | A45F 3/14 |
| 9,144,256 | B2 * | 9/2015 | Gheneva | A41D 1/06 |
| 9,999,291 | B1 * | 6/2018 | Putrello, Jr. | A45F 3/14 |
| 10,775,142 | B1 * | 9/2020 | Pineda | F42B 39/082 |
| D918,574 | S * | 5/2021 | Kumria | D3/215 |
| 11,273,064 | B2 * | 3/2022 | Ingimundarson | A61F 5/028 |
| D958,374 | S * | 7/2022 | Katoh | D29/100 |
| 11,561,065 | B1 * | 1/2023 | Hoffman | F41C 33/046 |
| 11,571,323 | B2 * | 2/2023 | Ingimundarson | A61F 5/022 |
| 2003/0110550 | A1 | 6/2003 | Guibord | |
| 2004/0226972 | A1 | 11/2004 | Cook | |
| 2005/0161479 | A1 * | 7/2005 | Licsko | A45F 3/14 224/270 |
| 2006/0000856 | A1 * | 1/2006 | West | A45F 5/00 224/148.2 |
| 2007/0017945 | A1 * | 1/2007 | Willis | A45F 5/021 224/270 |
| 2008/0047987 | A1 * | 2/2008 | Price | A47D 13/025 224/159 |
| 2009/0179055 | A1 * | 7/2009 | Estrellado | A45F 5/02 224/269 |
| 2011/0084107 | A1 * | 4/2011 | Reyes | A45F 5/02 224/666 |
| 2011/0144551 | A1 * | 6/2011 | Johnson | A61F 5/028 602/19 |
| 2012/0012630 | A1 * | 1/2012 | Lui | A41F 9/002 224/660 |
| 2019/0358808 | A1 | 11/2019 | Yoshitaka et al. | |
| 2020/0103073 | A1 | 4/2020 | Lennings et al. | |
| 2022/0265033 | A1 * | 8/2022 | Kumria | A45F 5/021 |
| 2023/0131059 | A1 * | 4/2023 | Mast | A45F 3/14 224/270 |

FOREIGN PATENT DOCUMENTS

| | | |
|---|---|---|
| DE | 202007014787 | 3/2008 |
| DE | 102006059890 | 6/2008 |
| DE | 202018107422 | 1/2019 |
| DE | 102019113913 | 11/2019 |
| EP | 2810579 A1 | 12/2014 |
| WO | 2012152863 A2 | 11/2012 |
| WO | 2015066793 | 5/2015 |

OTHER PUBLICATIONS

German Patent and Trademark Office, "Office Action" and English translation thereof issued in German patent application No. 10 2021127 397.8, dated Aug. 16, 2022, document of 13 pages.

* cited by examiner

Fig. 12

DEVICE FOR ASSISTANCE IN CARRYING LOADS

CROSS REFERENCE TO RELATED APPLICATIONS

This application claims priority to German Patent Application No. 10 2021 127 397.8, filed Oct. 21, 2021, the entirety of which is incorporated by reference.

FIELD OF APPLICATION

The application relates to a device for the support when bearing loads, with a hip belt.

BACKGROUND

It is known that the manual bearing of loads can put stress on the body, in particular on the back, of a person. Therefore, devices for load bearing support are known. DE 20 2007 014 U1 discloses a bearing belt which can be secured on a transport box or a beverage crate and placed over the shoulder in order to shift the weight of the transport box or the beverage crate onto the shoulder. DE 20 2018 107 422 U1 discloses a carrying aid with an angle element, which can be worn over the shoulder by means of a belt and shift the weight of a load to be borne onto the shoulder. However, by shifting the weight force onto the shoulder, stress is additionally placed onto the vertebral column.

DE 299 13 362 U1, for example, discloses a carrying aid with a belt that can be worn about the hip, which by means of loops, conducts the weight onto the shoulders of a person wearing it, wherein a movable front flap in the lower abdominal region of the person can be flipped out in the forward direction. Onto the front flap a load can be placed whereby the bearing of heavy loads can be supported. In the case of this carrying aid the weight is also displaced onto the shoulders.

WO 2015/066793 A1 discloses a further hip belt for support when bearing loads.

The disclosure addresses the problem of providing a device for support when bearing loads, which relieves the stress on the vertebral column when bearing loads and, moreover, also enables bearing loads using only one hand.

SUMMARY

The problem addressed by this disclosure is resolved through a device for load bearing support.

A device for load bearing support according to the disclosure with a hip belt having an inner side for placement in contact on a body of a person and an outer side, with a first end and a second end which are connectable with one another by means of a closure element, is distinguished thereby that the hip belt comprises a back element for placement in contact on a section of the back of a person, and that on the back element a first hip belt section is disposed, wherein on the outer side of the first hip belt section at least one, outwardly projecting first deposition element or elements is or are disposed at such distance from the back element that, when the belt is placed in contact on the body of the person, it or they is or are disposed laterally on the body of the person. A projecting deposition element enables the deposition of a load without additional manual handling. The lateral disposition of a deposition element on the body of a person enables the deposition of a load on the hip, wherein the weight force is diverted onto the hip. Additional stress exerted onto the vertebral column or the shoulders can thereby be avoided. Due to the deposition feasibility at the hip, the center of gravity, as a rule, is less strongly displaced such that the formation of lordosis can be decreased. By disposing the deposition element laterally on the body of the person, moreover, balance-stabilizing bearing using only one hand is enabled.

Furthermore, the disclosure provides for a second hip belt section to be disposed on the back element, wherein on the outer side of the second hip belt section at least one, outwardly projecting second deposition element or elements is or are disposed at such distance from the back element that, after the belt has been applied on the body of the person, it or they are disposed laterally of the body of the person and in particular on the other side as the first deposition element. This enables the support of bearing a load on one side as well as also on the other side of a person. Thereby unilateral stress on the person when bearing loads can be avoided.

When in the following a hip belt section is discussed, the first hip belt section and/or the second hip belt section are intended to be comprised therein. Likewise, the first deposition element and/or the second deposition element are intended to be comprised under the term deposition element.

The deposition element is fabricated of a rigid foam material, in particular of a rigid foam material having a hardness of more than 55 Shore. A rigid foam material enables a simple fabrication. Moreover, up to a certain degree, such rigid foam material can adapt to the anatomy of the body of the person. On the other hand, the rigid foam material can adequately support the bearing of the load.

The disclosure provides for the deposition element to be detachably disposed on the hip belt section. Interchanging of the deposition element, for example in order to be able to utilize a deposition element suitable for different loads to be borne, is thereby feasible in simple manner.

The deposition element is capable of being suspended by means of a hook in a corresponding recess on the hip belt section, or the deposition element is securable on the hip belt section by means of a dovetail guide. These two securement feasibilities enable the reliable securement and simple interchange.

The closure element is implemented as a zipper closure. Such closure element can readily be opened and closed and is non-bulky.

The hip belt is advantageously width-adjustable to enable the adaptation to different anatomical shapes of persons.

According to the disclosure at least the first hip belt section is disposed on the back element such that they are detachable. Such an embodiment can, on the one hand, enable the separation for purposes of cleaning; on the other hand, such embodiment can enable the adjustability of the width of the hip belt.

The first hip belt section is guided with a free end through a loop disposed on the back element, wherein the free end is fixable in different positions on a securement section of the hip belt section, by means of a hook-and-loop connection. Such embodiment enables varying in simple manner the width of the hip belt.

The back element has advantageously a greater height than the hip belt, whereby good stabilization of the back can be enabled.

A further development of the disclosure provides for a support belt to be disposed between an upper section of the back element and the first hip belt section and/or the second hip belt section, which support belt is in particular length-adjustable, by being guided with its free end through a loop disposed on the back element, wherein the free end is fixable in different positions on a securement section of the support belt, by means of a hook-and-loop connection. Such a support belt can distribute the forces acting onto the hip belt in particular in the region of the hip onto the back element and counteract the formation of lordosis.

The device according to the disclosure is expandible in order to enable further support functions, for example within the framework of an exoskeleton. An upper back element and/or two shoulder straps and/or two leg straps advantageously are in particular detachably disposed on the device in order to be able to enable such expended or additional functions.

BRIEF DESCRIPTION OF DRAWINGS

The disclosure will be explained in detail in conjunction with the following Figures. Therein depict.

DETAILED DESCRIPTION

FIGS. 1a to 7 show different views of a first embodiment example of a device 10 for load bearing support partly separately and partly in the applied condition on a person 100. Identical reference numbers denote in all Figures identical or functionally identical parts. For the sake of greater clarity not all reference numbers are provided in all Figures.

The device 10 comprises a hip belt 20 with an inner side 20a, to be applied in contact on a body of a person 100, and an outer side 20b. The hip belt 20 is herein in particular implemented substantially as an elongated element, which is intended to be placed around the waist of the person 100 and herein rests in particular on the hip of person 100 (cf. FIG. 1b). The hip belt 20 further comprises a first end 21 and a second end 22, both of which are connectable with one another by means of a closure element 25. The closure element 25 can, for example, be implemented as a hook-and-loop closure. The closure element 25 is preferably implemented as a zipper closure in order to be able to enable as precise a custom fit of the hip belt 20 as is feasible without any bulking elements.

Figure 1A:
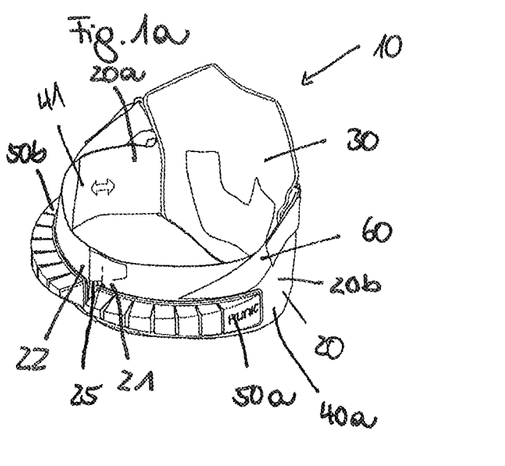
FIG. 1a a perspective view of a first embodiment example of a device according to the disclosure for load bearing support, FIG. 1b the device according to FIG. 1a in applied condition on a person, FIG. 2a a further perspective view of the device according to FIG. 1a, FIG. 2b the device according to FIG. 2a in applied condition on a person, FIG. 3a a view from the front onto the device according to FIG. 1a, FIG. 3b the device according to FIG. 3a in applied condition on a person, FIG. 4a a view from the back onto the device according to FIG. 1a, FIG. 4b the device according to FIG. 4a in applied condition on a person, FIG. 5a a side view of the device according to FIG. 1a, FIG. 5b the device according to FIG. 5a in applied condition on a person, FIG. 6 the person according to FIG. 5b with a load, FIG. 7 an exploded representation of the device according to FIG. 1a, FIG. 8 a view from the front onto a second embodiment example of a device according to the disclosure for load bearing support with add-ons to form an exoskeleton, FIG. 9 a view from the back onto the exoskeleton according to FIG. 8, FIG. 10 a perspective view of the exoskeleton according to FIG. 8, FIG. 11 an exploded representation of the exoskeleton according to FIG. 8 in applied condition on a person and FIG. 12 the exoskeleton according to FIG. 8 in applied condition on a person.
Figure 1B:
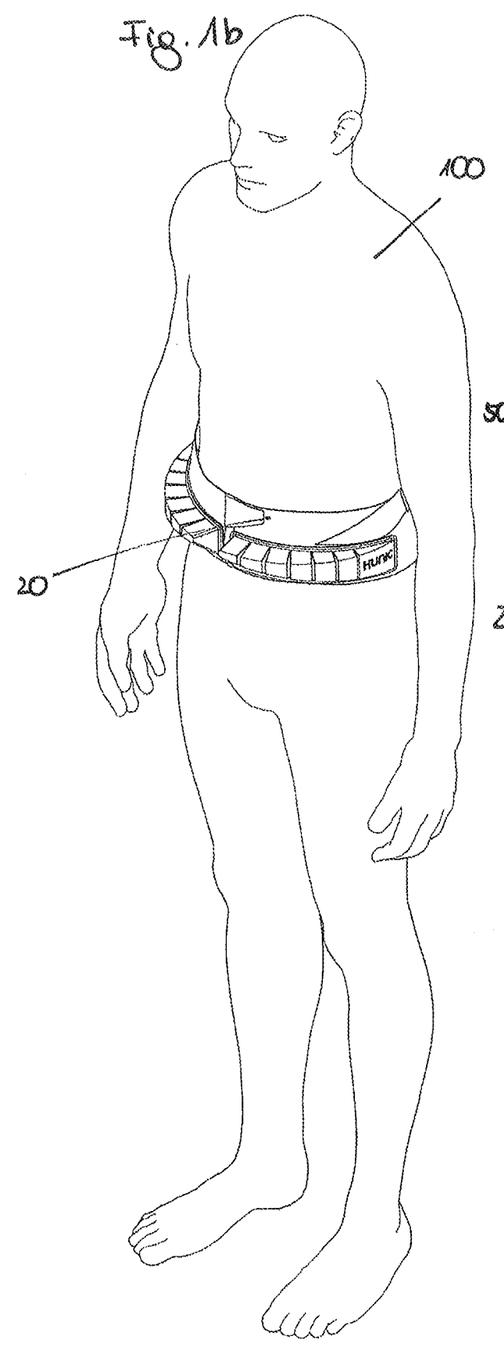
Figures 2A, 2B:
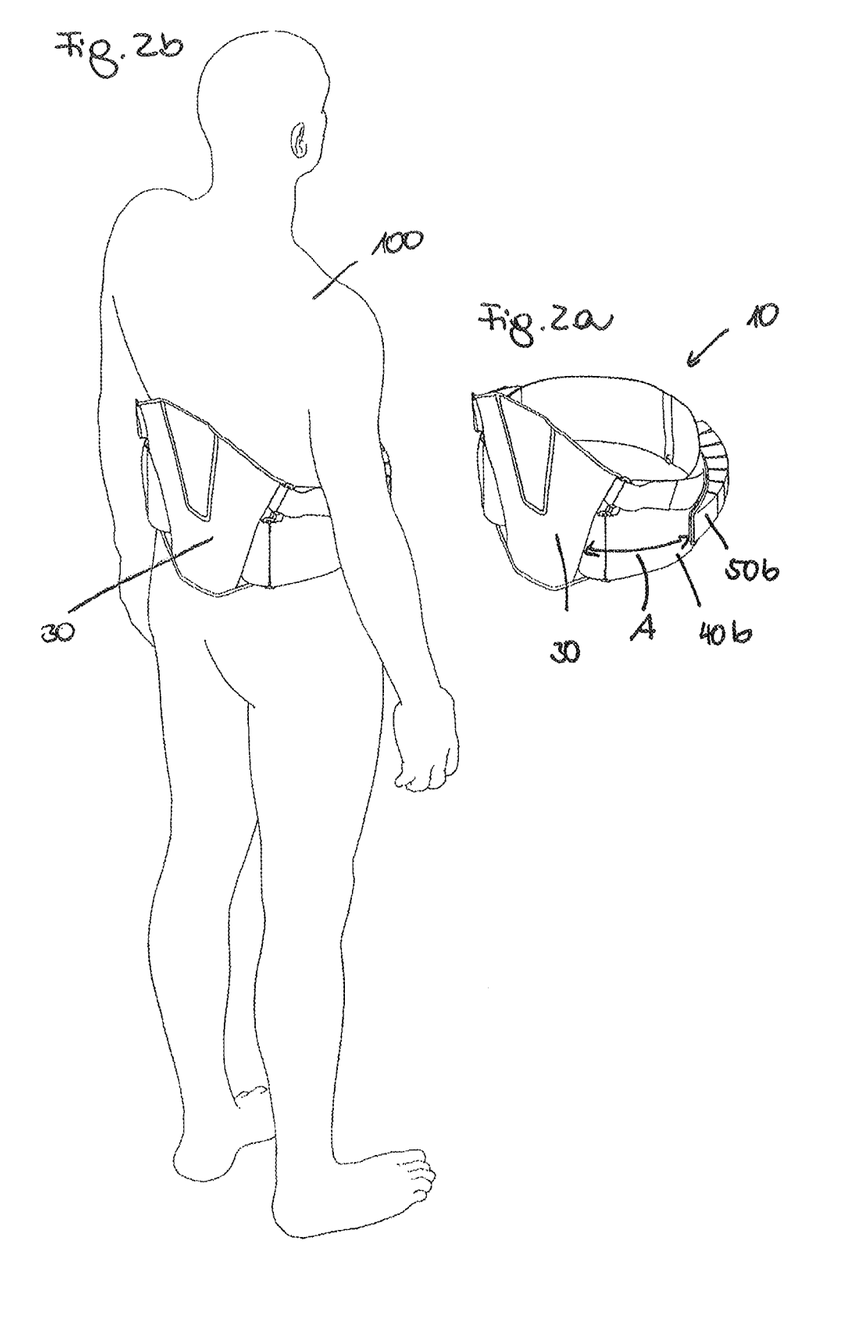
Figure 3A:
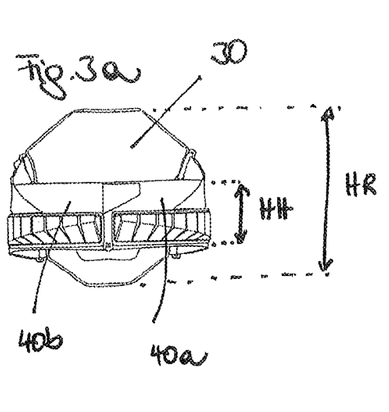
Figure 3B:
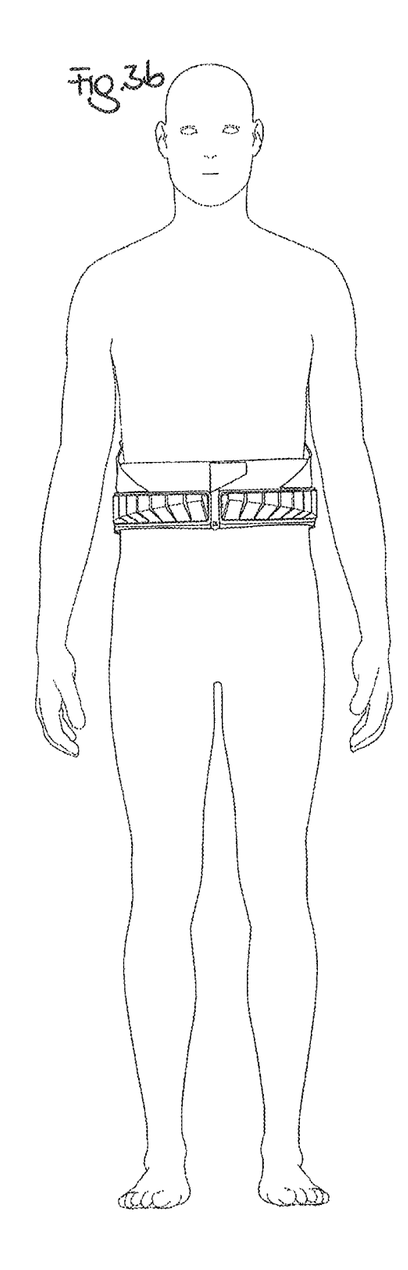
Figure 4A:
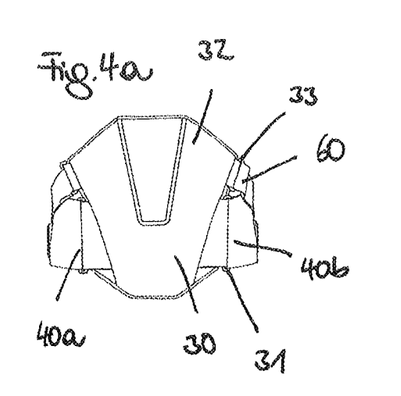
Figure 4B:
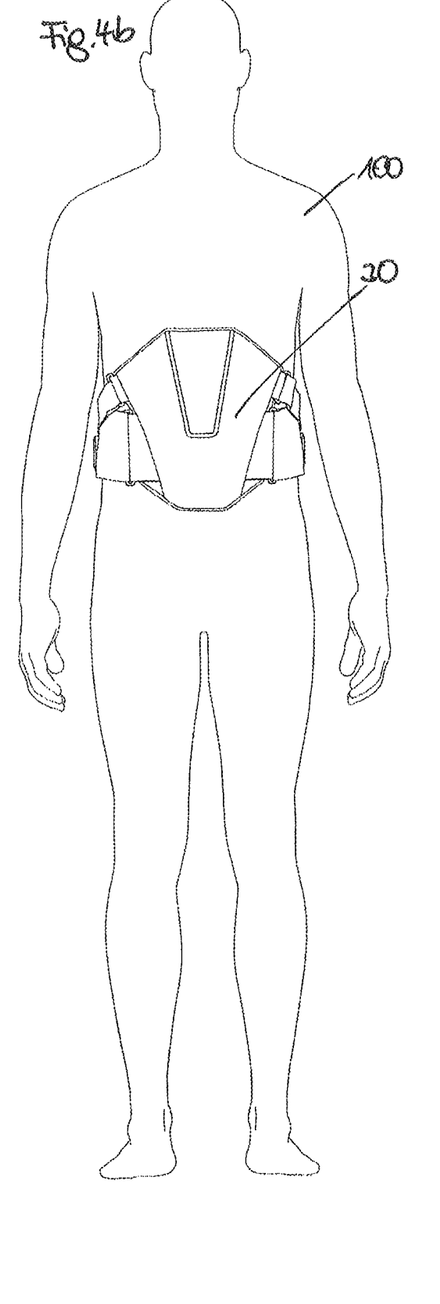
Figure 5A:
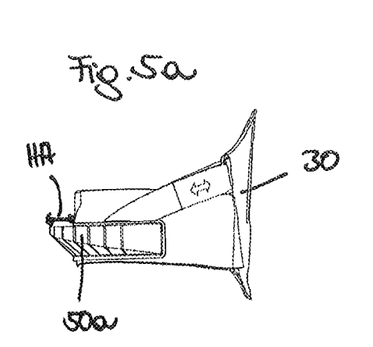
Figure 5B:
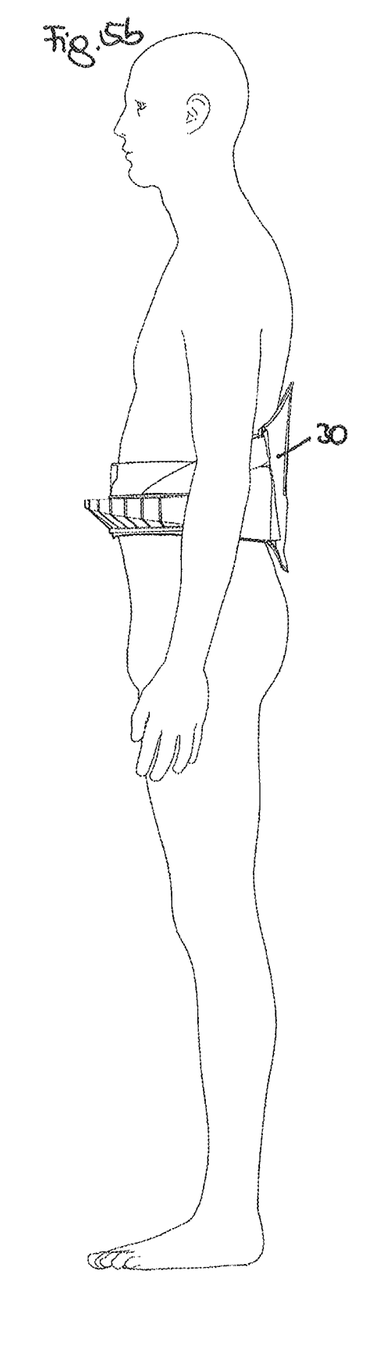

The hip belt 20 comprises a back element 30 for application in contact on a section of the back of the person 100 (cf. in particular FIGS. 2a and 2b). The back element 30 forms in particular a reinforced section for the support of the vertebral column and to be able to counteract the formation of lordosis under stress. The back element 30 can be implemented for example as a hard shell. The back element 30 can thereby be implemented with the least feasible wall thickness of less than 2 cm, in another embodiment is less than 1 cm, in order to add the least feasible bulk.

The back element 30 can at least in sections be fabricated of a shape-elastic material. The shape-elastic material can be, for example, a metal or a synthetic material. The shape-elastic material has a modulus of elasticity of more than 600 $N/mm^2$, in another embodiment a modulus of elasticity of more than 1000 $N/mm^2$, for example a modulus of elasticity of 5000 $N/mm^2$. If the back element 30 is sectionally fabricated of a shape-clastic material, it can be fabricated, for example, of a textile fabric with an embedded element of a shape-elastic material.

On the back element 30 a first hip belt section 40a is disposed. The first hip belt section 40a can be fabricated of an elastic textile fabric. The first hip belt section 40a comprises the first end 21 of the hip belt 20 and comprises furthermore a free end 41 with which the first hip belt section 40a is secured on the back element 30. It is feasible for the second end 22 to be implemented on the back element 30 and the first end 21 for closing the hip belt 20 to be secured on the second end 22 disposed on back element 30. However, in another embodiment a second hip belt section 40b to be disposed on the back element 30. The second hip belt section 40b can be fabricated of an elastic textile fabric. The second hip belt section 40b comprises the second end 22 of hip belt 20 and comprises additionally a free end 41 with which the second hip belt section 40b is secured on the back element [30]. Such implementation enables in particular the disposition of the closure element 25 approximately in the region in front of the navel of the person 100. Such implementation furthermore enables in particular a symmetric structuring of hip belt 20.

The hip belt 20 can be width-adjustable. This can be realized through the appropriate implementation of the closure element 25, for example in the manner of a belt or by means of a hook-and-loop closure.

Alternatively, or additionally, at least the first hip belt section 40a, in another embodiment the first hip belt section 40a and the second hip belt section 40b, can be detachably disposed on the back element 30. For this purpose, the free end 41 of the hip belt section 40a, 40b can be guided through a loop 31 disposed on the back element 30. The loop 31 can be implemented as a metal ring, for example, which can, in particular, be of elongated shape (cf in particular FIG. 7). The free end 41 can be fixable in different positions on a securement section 42 of the hip belt section 40a, 40b. For this purpose, a hook-and-loop connection can be provided, wherein on the free end 41 a hook section and on the securement section 42 a loop section, or conversely, can be provided. In this way the width can be simply varied by the person 100. If both hip belt sections 40a, 40b are in this manner secured to be detachable from the back element 30, the width can be varied in particular thereby that the closure element 25 for all widths is disposed in the region of the navel of the person 100 and a symmetric disposition of the hip belt 20 on the person 100 is feasible.

On the outer side 20b of the first hip belt section 40a at least one outwardly projecting first deposition element 50a is disposed at such distance A from the back element 30 that in the applied condition in contact on the body of person 100 it is disposed laterally on the body of the person 100, in particular approximately in the region above the pelvic bone. In the direction perpendicularly to the outer side 20b of hip belt 20, the deposition element 50a can extend along the hip belt section 40a up into the proximity of the closure element 25. The deposition element 50a can extend along the hip belt section 40a up into the proximity of the closure element 25. The deposition element 50a can have a height HA of a few centimeters, for example in the range of 3 cm to 15 cm, in particular in the range of 6 cm to 10 cm. The deposition element 50a can herein be disposed on a base element 50a-1 {or?} several projections 50a-2 in order to be able to enable better adaptation of the deposition element 50a to different widths of the hip belt 20. It is also feasible for several individual deposition elements 50a to be disposed adjacently to one another in this region. Of advantage is that the deposition element 50a after it is applied on the person 100 is located in the region above the pelvic bone in order to be able to enable the deposition of a load to be borne with one arm in the region of the hip.

Figure 6:
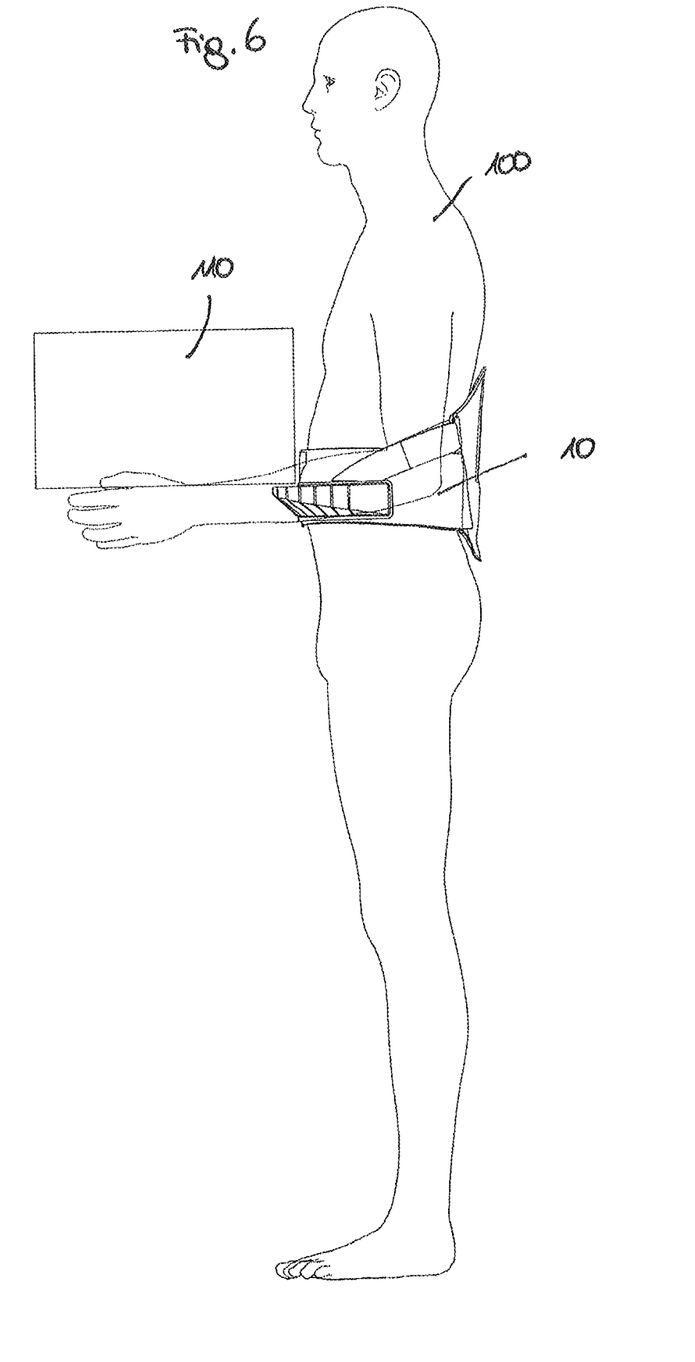
Figure 7:
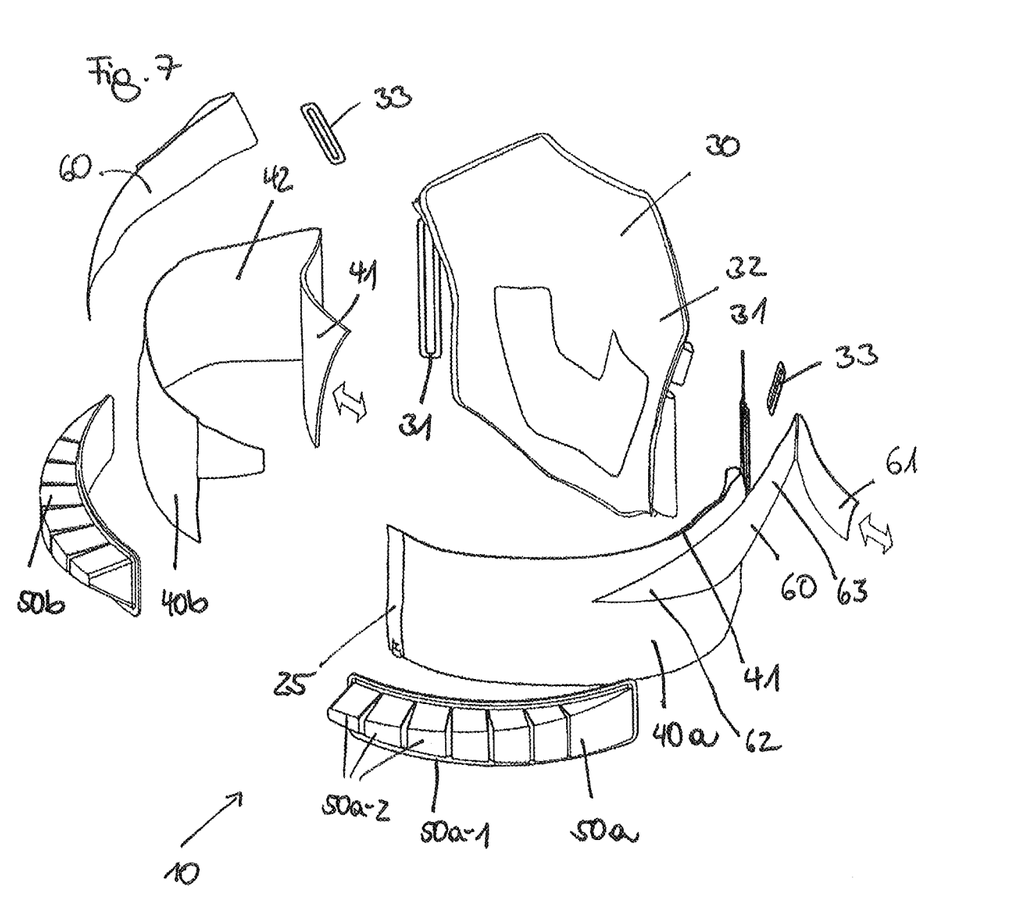
Figure 8:
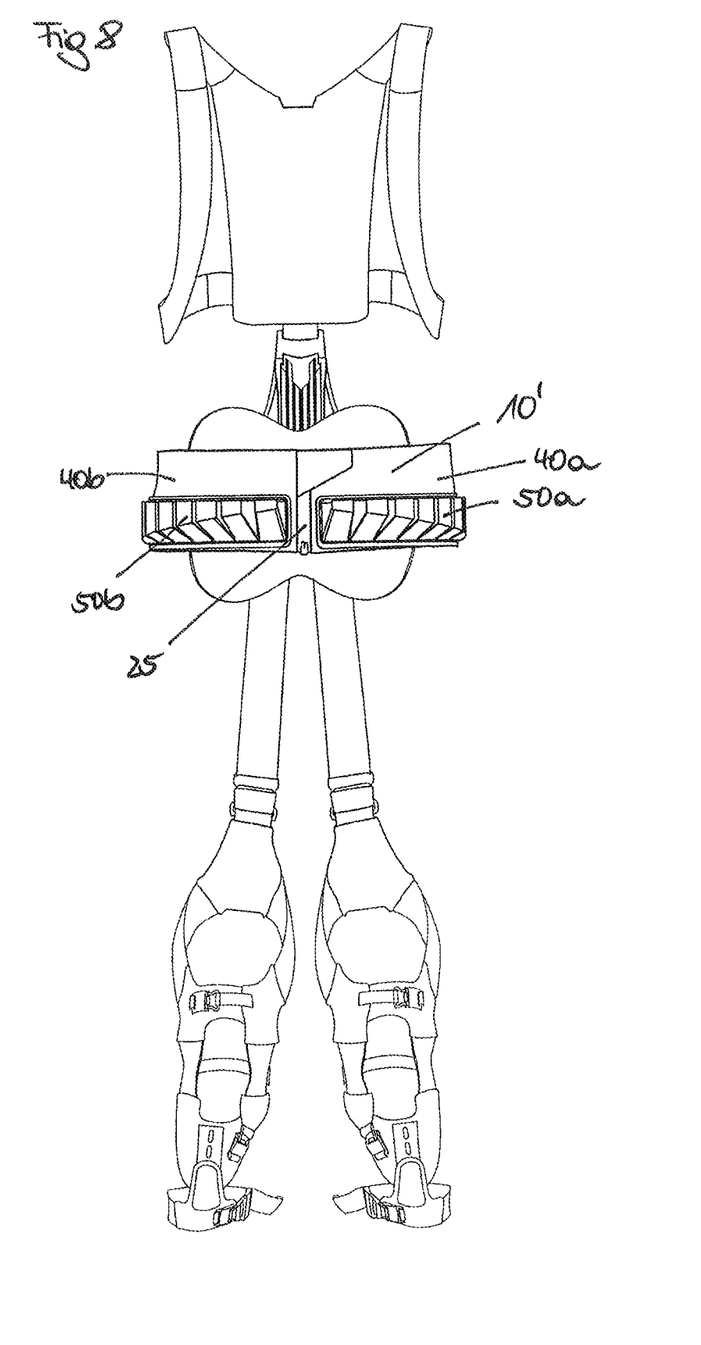
Figure 9:
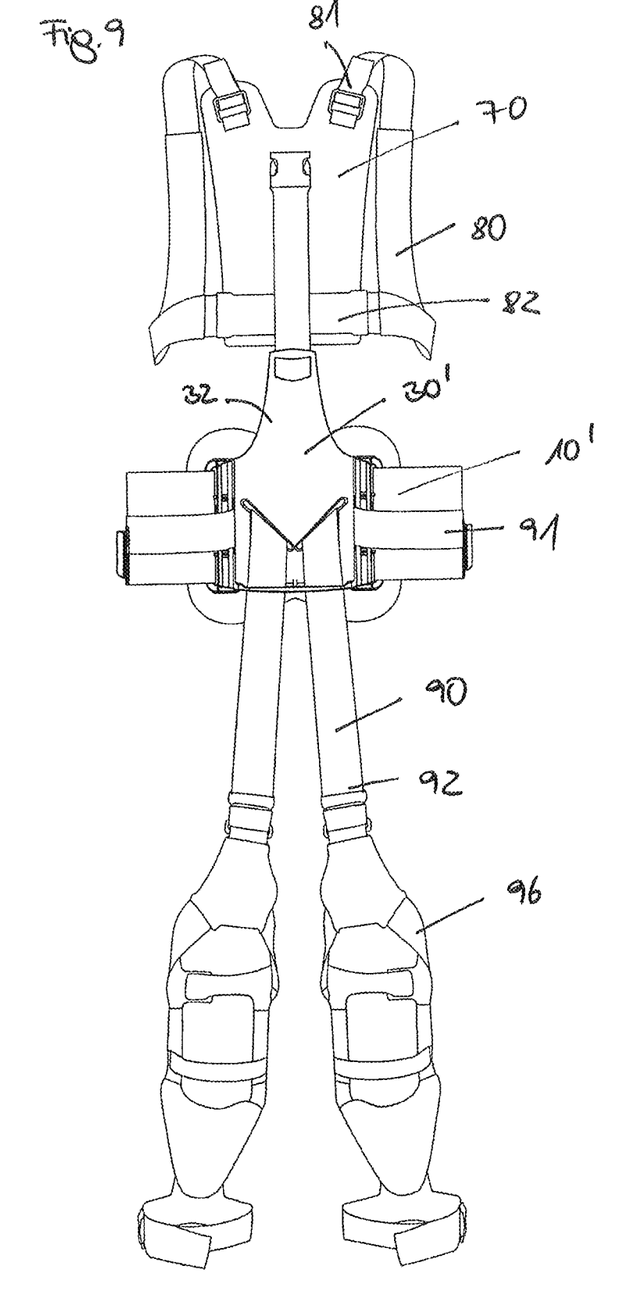
Figure 10:
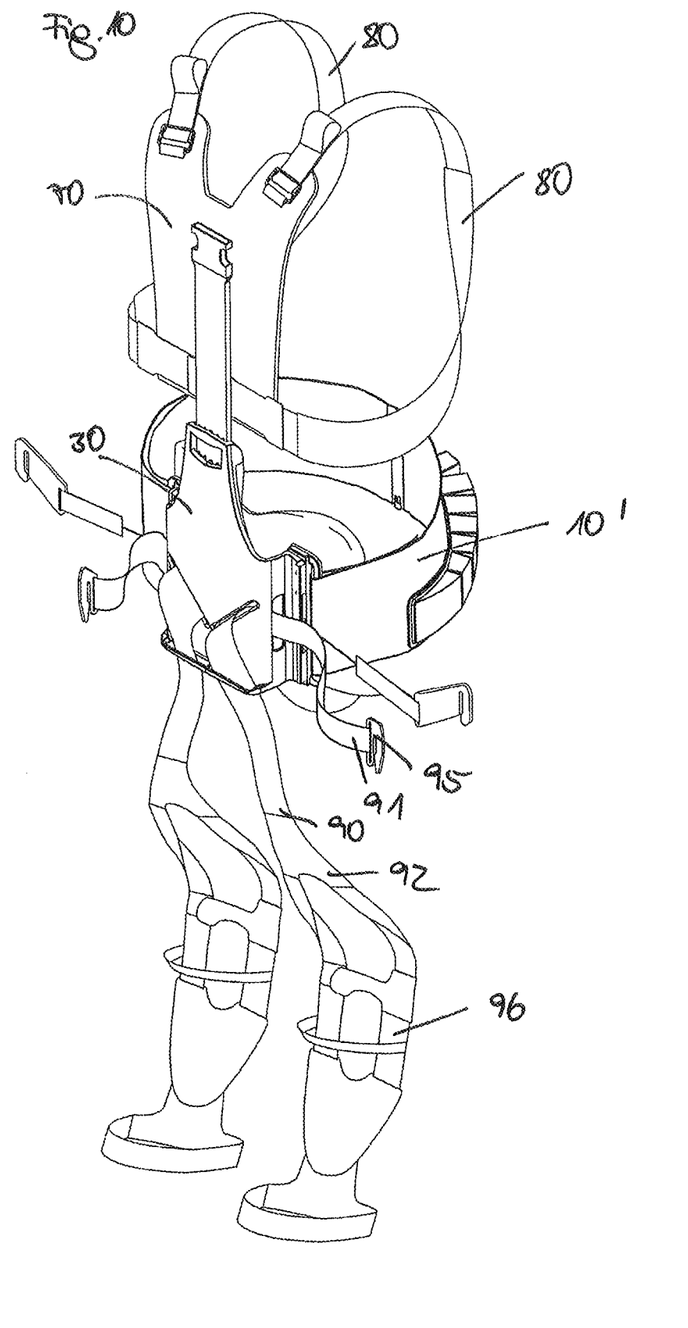
Figure 11:
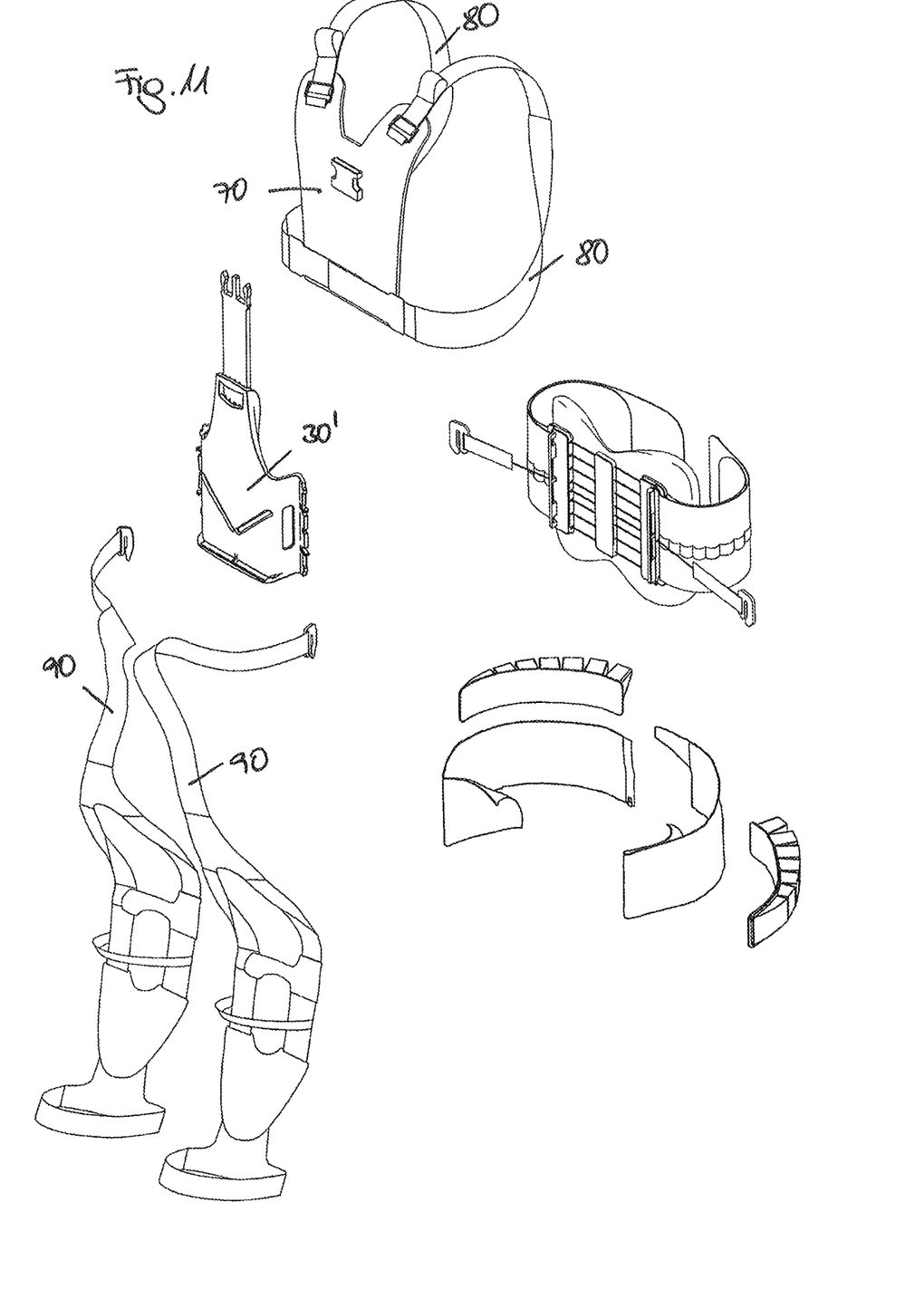

As is discernible in FIG. 6, the implementation in such manner in which the deposition element 50a, 50b extends up into the region in front of the abdomen of the person 100 enables, on the one hand, bearing a load 110 with both hands while bracing or stabilizing on the deposition element 50a, 50b in front of the abdomen; however, on the other hand, enables also the single-handed bearing of load 110 while bracing either on the deposition element 50a on the left side of the person 100 or while bracing on the deposition element 50b on the right side of the person 100.

The deposition element 50a can be fabricated of a rigid foam material, in particular of a rigid foam material having a hardness of more than 55 Shore.

The deposition element 50a can be disposed on the hip belt section 40a such that it is detachable. For this purpose, the deposition element 50a can be hingeable, for example by means of a hook into a corresponding recess on the hip belt section 40a, or the deposition element 50a can be securable by means of a dovetail guide on the hip belt section 40a.

Provided a second hip belt section 40b is available, on the outer side 20b of the second hip belt section 40b at least one, outwardly projecting second deposition element or elements 50b is or are disposed at such distance A from the back element 30 that, after it is applied on the body of the person 100, it is disposed laterally on the body of the person 100 and, in particular, on the other side as the first deposition element 50a. In other respects, the same explanations apply to the second deposition element 50b as were presented regarding the first deposition element 50a.

The back element 30 can be of greater height HR than the hip belt 20. For example, the hip belt 20 can have a height HH in the range of approximately 10 cm to 15 cm, for example a height HH of approximately 12 cm. The back element 30 can have a height HR of 20 cm to 35 cm.

Between an upper section 32 of the back element 30 and the first hip belt section 40a a support belt 60 is disposed which is, in particular, length-adjustable. The support belt [60] comprises a free end 61 which can be guided, in particular, through a loop 33 disposed on the back element 30, wherein the free end 61 is fixable, by means of a hook-and-loop connection, in different positions on a securement section 63 of the support belt [60]. The loop 33 can be implemented for example as a metal ring which has, in particular, an elongated shape (cf in particular FIG. 7). The support belt 60 can be fixed on the first hip belt section 40a with a fixed end 62.

Between the upper section 32 of the back element 30 and the second hip belt section 40b a like support belt 60 can likewise be disposed.

The device 10 can be expanded into an exoskeleton using additional components.

FIGS. 8 to 12 show different views of a second embodiment example of a device 10' for load bearing support, which, using additional components, has been expanded into an exoskeleton. The device 10' herein differs from the device 10, described above in conjunction with FIGS. 1 to 7, substantially by the implementation of the back element 30 and thereby that no support belts 60 are provided.

The device 10' comprises a back element 30' which, in its upper section, can enable the linkage to an upper back element 70. The upper back element 70 can herein be of such length that, together with the back element 30', it forms an element which, in the condition applied on the person 100, extends from the region of the pelvis up into the region of the upper back or neck. The upper back element 70 can, in particular, also rest at its end facing away from the hip belt 20 on the shoulders of the person 100. The back element 30' and the upper back element 70 can be length-adjustably fixable with respect to one another.

The upper back element 70 can comprise two shoulder straps 80 each comprising a first end 81 and a second end 82. As shoulder straps 80 are to be understood in the following those elements which, when the upper back element 70 is applied on the person 100, fix the upper back element 70 such that it is in contact on the back of the person [100]. The shoulder straps 80 can be disposed on the back element 30' such that they are length-adjustable. The shoulder straps 80 can be fabricated of a strap material, for example of a textile tape.

Figure 12:
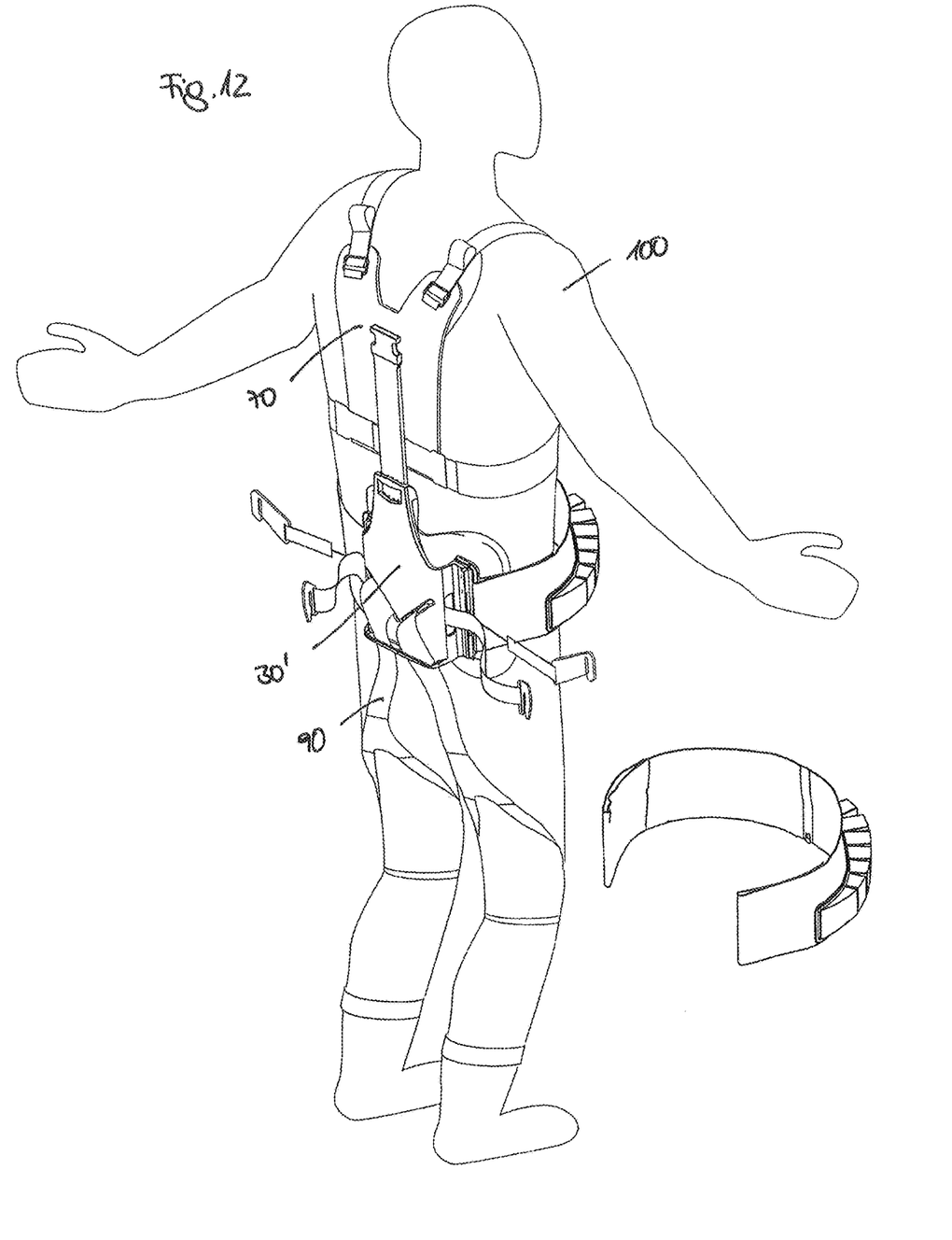

On the hip belt 20, in particular on the back element 30', additionally or alternatively to the upper back element 70, two leg straps 90 can be disposed in particular such that, when the device is applied on the person 100, they extend from the hip across the buttocks of the person 100 in contact on the legs (cf FIG. 12). The leg straps 90 comprise a first end 91 and a second end 92. The leg straps 90 are detachably disposed with the first end 91 on the hip belt 20, in particular on the outer side 20b of the hip belt 20, for example by means of a hook 95, a snap buckle or alternatively in the manner of a closure of a belt or by means of a hook-and-loop closure or other closures. The leg straps 90 are in particular implemented such that they are length-adjustable.

At the second end 92 of the leg strap 90 can be disposed a knee element 96 in order to be able to fix the leg strap 90.

The leg straps 90 and/or the knee element 96 can at least in sections be fabricated of an elastomer. The elastomer can have a modulus of elasticity of less than 600 N/mm$^2$, in another embodiment a modulus of elasticity of less than 150 N/mm$^2$, in another embodiment a modulus of elasticity of less than 100 N/mm$^2$, in another embodiment a modulus of elasticity of approximately 30 N/mm$^2$.

The leg straps 90 can support straightening-up after bending or after squatting of the person 100.

LIST OF REFERENCES

10 Device
10' Device
20 Hip belt
20a Inner side
20b Outer side
21 First end
22 Second end
25 Closure element
30 Back element
30' Back element
31 Loop
32 Upper section
33 Loop
40a First hip belt section
40b Second hip belt section
50a First deposition element
50a-1 Base element
50a-2 Projection
50b Second deposition element
41 Free end
42 Securement section
60 Support belt
61 Free end
62 Fixed end
70 Upper back element
80 Shoulder strap
81 First end
82 Second end
90 Leg strap
91 First end
92 Second end
95 Hook
96 Knee element
100 Person
110 Load
A Distance
HH Height
HR Height
HA Height

The invention claimed is:

1. A device for load bearing support, comprising:
a hip belt comprising:
an inner side that contacts a body of a person when the hip belt is worn by the person;
an outer side;
a first end;
a second end, wherein the first end and second end releasably connect with one another;
a back support that contacts a section of a back of the person;
a first hip belt section disposed on the back support;
at least one outwardly projecting deposition element disposed on an outer side of the first hip belt section and at a distance from the back support such that after the hip belt is placed in contact with the body of the person, the at least one outwardly projecting deposition element is disposed laterally on the body of the person;
a support belt disposed between an upper section of the back support and the first hip belt section, wherein the support belt has an adjustable length, wherein the support belt is guided with a support belt free end through a loop disposed on the back support, wherein the support belt free end is fixable in different positions on a securement section of the support belt.

2. The device as in claim 1, further comprising zipper that releasably connects the first end and second end with one another.

3. The device as in claim 1, wherein a width of the hip belt is adjustable.

4. The device as in claim 1, wherein the back support has a greater height than the other parts of the hip belt.

5. The device as in claim 1, further comprising:
a second hip belt section disposed on the back support; and
at least one additional outwardly projecting deposition element disposed on an outer side of the second hip belt section and at a distance from the back support such that after the hip belt is placed in contact with the body of the person, the at least one additional outwardly projecting deposition element is disposed laterally on the body of the person and opposing the at least one additional outwardly projecting deposition element.

6. The device as in claim 5, wherein the at least one outwardly projecting deposition element of the first hip belt section is detachably disposed on the first hip belt section and the at least one additional outwardly projecting deposition element of the second hip belt section is detachably disposed on the second hip belt section.

7. The device as in claim 5, wherein the at least one outwardly projecting deposition element and the at least one additional outwardly projecting deposition element are hingeable with a hook into a corresponding recess on the first hip belt section and/or the second belt section.

8. The device as in claim 5, wherein the at least one outwardly projecting deposition element and the at least one additional outwardly projecting deposition element are securable on the first hip belt section and/or the second hip belt section with a dovetail guide.

9. The device as in claim 5, wherein the first hip belt section and the second hip belt section are guided with a respective free end through a loop disposed on the back support, wherein the respective free end is fixable in different positions on a securement section of the first hip belt section with a hook-and-loop fastener.

10. The device as in claim 5, further comprising an upper back support, two shoulder straps, and two leg straps disposed detachably on the hip belt.

11. The device as in claim 5, wherein the support belt is disposed between an upper section of the back support and each of the first hip belt section and the second hip belt section.

12. The device as in claim 5, wherein the at least one outwardly projecting deposition element and the at least one additional outwardly projecting deposition element comprise a rigid foam material.

13. The device as in claim 12, wherein the rigid foam material has a hardness of more than 55 Shore.

14. The device as in claim 5, wherein the first hip belt section is detachably disposed on the back support.

15. The device as in claim 14, wherein the second hip belt section is detachably disposed on the back support.

* * * * *